United States Patent [19]

Falcoff et al.

[11] Patent Number: 4,511,251

[45] Date of Patent: Apr. 16, 1985

[54] APPARATUS AND PROCESS FOR MEASURING THE COLOR OF PAINTS

[75] Inventors: Allan F. Falcoff, Lake Orion; Eric Mikkelsen, Pontiac; Allan B. J. Rodrigues, Bloomfield Hills, all of Mich.

[73] Assignee: E. I. Du Pont de Nemours and Company, Wilmington, Del.

[21] Appl. No.: 440,572

[22] Filed: Nov. 10, 1982

[51] Int. Cl.³ .............................................. G01N 21/05
[52] U.S. Cl. ..................................... 356/246; 356/410
[58] Field of Search ......................... 356/410, 246, 411

[56] References Cited

U.S. PATENT DOCUMENTS 2,436,511 2/1948 Flatford et al. ...................... 356/246
3,020,795 2/1962 McKinney et al. .................. 356/246
3,773,424 11/1973 Selgin .............................. 356/246 X Primary Examiner—F. L. Evans
Attorney, Agent, or Firm—Hilmar L. Fricke

[57] ABSTRACT

An apparatus for the inspection of fluids, particularly paints, having a housing with a cavity and enclosed with a light transmitting window and having an insert member positioned in the cavity which provides a fluid chamber where fluid flows by the window and wherein the flow is laminar and undirectional. This provides a view area of the liquid whose color parameter can be accurately measured by a colorimeter of spectrophotometer. The apparatus is particularly useful in the manufacture of paints so that the color of the paint being made can be accurately matched to a standard color.

2 Claims, 3 Drawing Figures

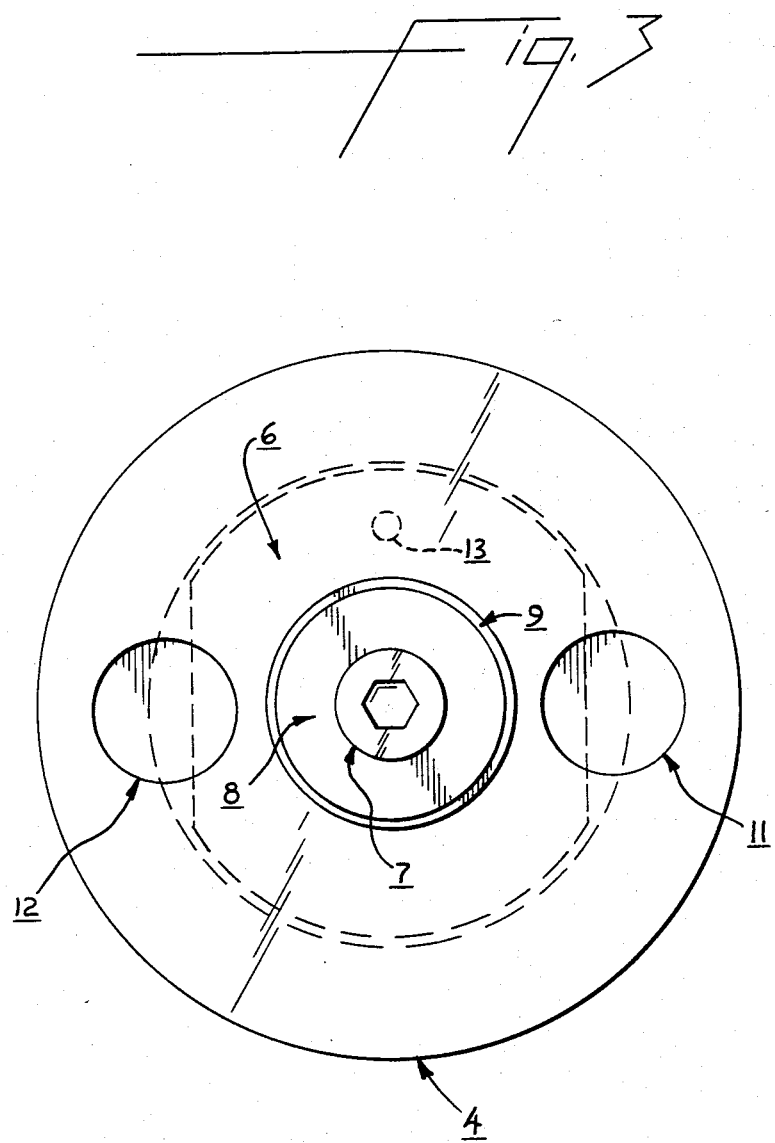

APPARATUS AND PROCESS FOR MEASURING THE COLOR OF PAINTS

BACKGROUND OF THE INVENTION

This invention is related to an apparatus for the inspection of fluids. In particular, the invention is related to an improved apparatus for measuring the color of a paint flowing through the apparatus.

In the manufacture of paints, one problem is to match the color of the paint as it is being made to a standard paint color. Either a colorimeter or spectrophotometer usually is used to measure color parameters of the paint being made. Colorants such as pigment dispersions and tints are added to the paint until the color parameters match those of the standard paint color. McKinney et al. U.S. Pat. No. 3,020,795 issued Feb. 13, 1962 shows an apparatus which can be used to inspect paints. However, this apparatus is inadequate since the design of the apparatus results in a dark spot in the center of the viewing window of the apparatus caused by paint being forced under pressure up through a tapered passage and impinged on the viewing window. A colorimeter focused near the edge of the viewing window and a colorimeter focused on the center of the window will have different readings making it impossible to accurately match the paint being made to a standard paint color.

Also, there is a particular problem with paints containing metallic flake pigments. These pigments must be flowing in a parallel relationship to the viewing window and should not be tumbling in order to provide an instrument such as a colorimeter with consistent readings. There is a need for a viewing apparatus which will provide a paint stream of a uniform color without turbulent motion so that accurate instrumental readings can be taken.

SUMMARY OF THE INVENTION

An apparatus for inspection of fluids having the following components:
- a housing having a cavity therein,
- a light transmitting window enclosing one end of the cavity,
- a cylindrical insert member positioned in the cavity having a flat horizontal surface area and being in a closely spaced relationship with the window providing a fluid chamber where fluid flows between the window and the flat surface area of the insert member at a uniform velocity across the window and the cylindrical insert member having a vertical flat surface on opposite sides of the insert member which in combination with the housing forms an inlet channel to the fluid chamber and an outlet channel from the fluid chamber,
- a fluid inlet connected to the inlet channel and fluid outlet connected to the outlet channel in the housing in communication with the fluid chamber,
- wherein the fluid flows through the inlet and through the inlet channel into the fluid chamber and out of the chamber through the outlet channel and the outlet and the flow of fluid through the chamber is a undirectional laminar flow.

A process for measuring the color of a paint using the above apparatus and colorimeter also is a part of this invention.

BRIEF DESCRIPTION OF THE DRAWINGS

FIG. 3 shows the top view of the apparatus.

DETAILED DESCRIPTION OF THE INVENTION

In general, the apparatus of this invention can be used to inspect a wide variety of fluids but is designed particularly to measure the color of paints since it is designed to provide a paint stream of a uniform color so that accurate color measurements can be made. The flow of the paint through the viewing area of the apparatus is in the laminar flow region which provides alignment of any flake pigments in the paint in the viewing area to insure uniform color measurements of the paint.

Figure 1:
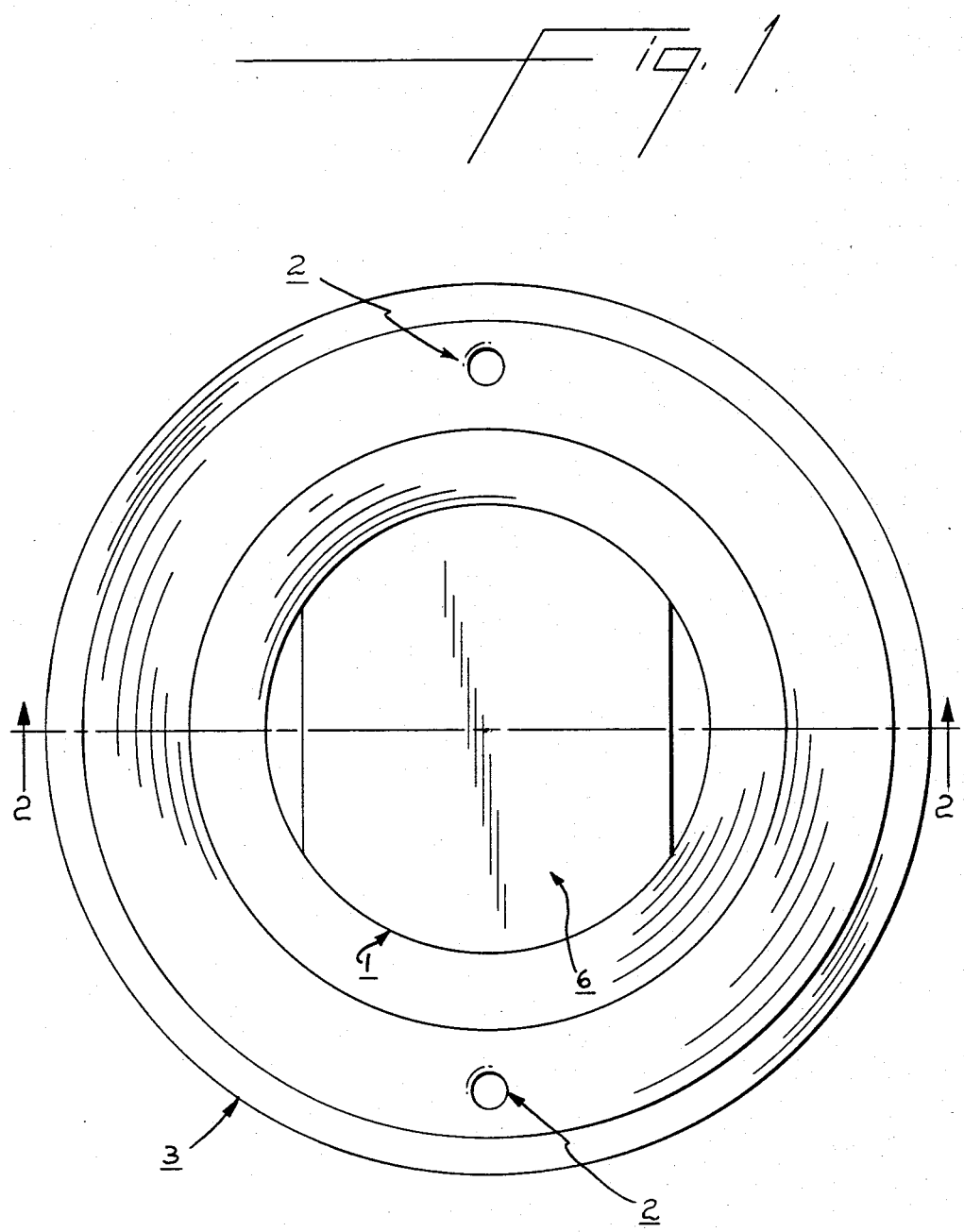
FIG. 1 shows the bottom view of the apparatus.

FIG. 1 shows the top view of the apparatus. A viewing window 1, usually of quartz glass, is held in place by a cap 3 having two recessed holes 2 for a spanner wrench which is used to tighten and loosen the cap 3. The exterior surface of the cap 3 is coated with a non-reflective material such as a flat black paint to reduce scattering of outside light which would give erroneous color measurements.

The interior of the viewing window 1 can be coated with a thin layer of a fluorocarbon polymer which substantially reduces adherence of pigment particles to the window and thereby provides a clear viewing window for a relatively long time period before removal and cleaning are required.

Figure 2:
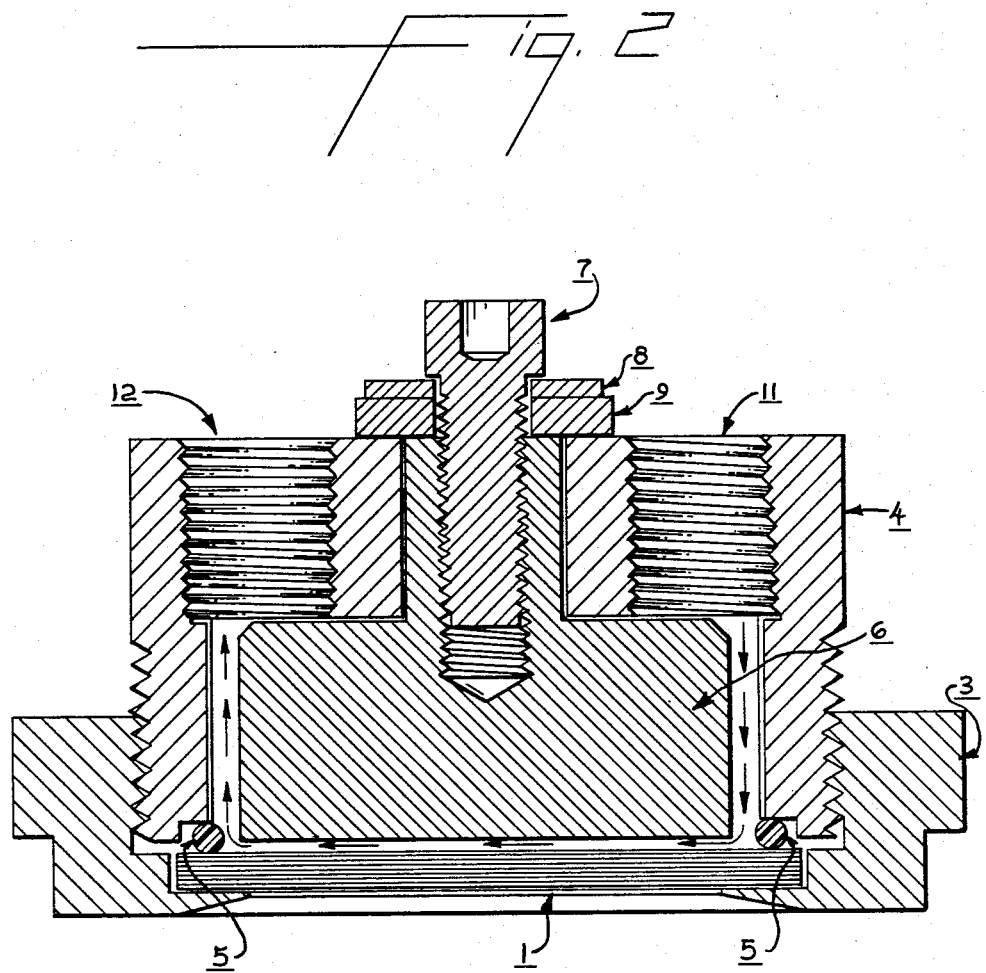
FIG. 2 shows a cross sectional view taken along line 2—2 of FIG. 1 showing one arrangement of the apparatus.

FIG. 2 shows a cross section taken along line 2—2 of FIG. 1 and shows one arrangement of the apparatus. The cap 3 is screwed onto the body 4, and holds the viewing window 1 in place. An O-ring gasket 5, usually of a fluorocarbon polymer, forms a seal between the viewing window 1 and the body 4. An insert 6, is positioned in a cavity in the body 4 and is in a close relationship with the viewing window 1 and forms a fluid chamber. FIG. 1 shows a top view of insert 6 as it is positioned in the apparatus. The distance between the viewing window 1 and the flat portion of the insert 6 is about 1/32 to ⅛ inch. The distance is sufficient to insure than the paint circulating through the apparatus completely hides the flat portion of insert 6. The insert 6 is held in place in the body 4 by a cap screw 7 and a metal washer 8 and a fluorocarbon polymer washer 9 are used to seal the insert 6 in the body 4. The body 4 is provided with an inlet opening 11 and an outlet opening 12 which are usually threaded to receive an inlet and outlet pipe, not shown.

FIG. 3 shows the bottom view of the apparatus. The body 4 has an inlet opening 11 and an outlet opening 12 and holds the insert 6, shown by a broken line, in place by cap screw 7 which is sealed by a fluorocarbon polymer washer 9 and steel washer 8. The relative position of the insert 6 in relation to the inlet opening 11 and the outlet opening 12 are shown. The second circle of broken lines surrounding the insert 6 shows the outline of the cavity in the body 4. To insure that the insert 6 is properly aligned in the cavity of the body 4, a pin 13 is positioned in a hole in the body 4 and in a hole in the insert 6. The proper alignment of insert 6 assures undirectional fluid flow through the fluid chamber from the inlet opening 11 to the outlet opening 12.

The cap 3, insert 6, body 4 are made of a material which is non-reactive with the fluid such as a paint that is being passed through the apparatus. Typically, these components are made of brass or stainless steel.

In the operation of the apparatus, (referring to FIG. 2) a fluid such as paint is pumped into the apparatus through inlet 11 and into a fluid chamber formed by the insert 6 and the viewing window 1 and out throught the outlet 12. The arrows show the direction of fluid flow through the apparatus. The chamber is designed to provide fluid flow through the chamber in the laminar region. The Reynolds No. of the fluid flowing through the chamber is about 25-2000 and preferably about 50-200.

A Reynold's Number is a dimensionless quantity that measures flow and is well known in the art.

Reynold's Number $N_{Re} = D\rho V/\mu$ where
D is the diameter of a cross sectional area or the equivalent diameter;
V is the linear velocity of the fluid;
$\mu$ is the absolute viscosity of the fluid;
$\rho$ is the density of the fluid.

For a typical apparatus in which the opening between the viewing window and the flat portion of insert is 3/32 inch and the width of the insert is 1.625 inches and a typical automotive paint is being pumped through the apparatus, the following is illustrative of a Reynold's Number calculation:

Area = 3/32 in. × 1.625 in. = 0.152 in.$^2$ = 0.001 ft.$^2$ $$D_{(equivalent)} = \left[\frac{4A}{\pi}\right]^{\frac{1}{2}} = \left[\frac{4(.001 \text{ ft.}^2)}{\pi}\right]^{\frac{1}{2}} = 0.0357 \text{ ft.}$$

$$V = 0.5 \text{ gallons/minute} = \frac{0.0011 \text{ ft.}^3}{\text{sec.}} \times \frac{1}{0.001 \text{ ft.}^2} = 1.053 \text{ ft./sec.}$$

-continued $\rho = 60$ lb./ft.$^3$
$\mu = 0.0336$ lb./ft. sec.

$$N_{Re} = \frac{(0.0357 \text{ ft.})(60 \text{ lb./ft.}^3)(1.053 \text{ ft./sec.})}{0.0336 \text{ lb./ft. sec.}} = 69.0$$

The apparatus can be used in a variety of chemical processes in which color of the resulting product is measured but is preferably used in a paint manufacturing or paint mixing process. Typically, the apparatus is connected to a pipe coupled to a mixing vessel and after the paint is thoroughly mixed in the vessel, the paint is circulated through the apparatus and the color parameters of the paint are determined, usually with a colorimeter.

We claim:

1. An apparatus for inspection of a fluid comprising:
   a cylindrical housing having a cylindrical cavity therein,
   a light transmitting window enclosing one end of the cavity,
   a cylindrical insert member positioned in said cavity having a flat horizontal surface area and being in a closely spaced relationship with the window providing a fluid chamber where fluid flows between said window and the flat surface area of said insert member at a uniform velocity across the window and said cylindrical insert member having a vertical flat surface on opposite sides of the insert member which in combination with the housing forms an inlet channel to the fluid chamber and an outlet channel from the fluid chamber,
   a fluid inlet connected to the inlet channel and a fluid outlet connected to the outlet channel in communication with said fluid chamber, wherein fluid flows through the inlet and through the inlet channel into the fluid chamber and out of the chamber through the outlet channel and the outlet, the flow of fluid through the chamber being an undirectional laminar flow and having a Reynold's Number of 50-200.

2. The apparatus of claim 1 in which the window is of quartz glass.

* * * * *